(12) United States Patent
Bruijns

(10) Patent No.: US 7,447,296 B2
(45) Date of Patent: Nov. 4, 2008

(54) MEDICAL IMAGING DEVICE HAVING MEANS FOR RENDERING THE DETECTOR ORIENTATION AND THE DISPLAY ORIENTATION ESSENTIALLY EQUAL

(75) Inventor: Antonius Johannes Cornelius Bruijns, Eindhoven (NL)

(73) Assignee: Koninklijke Philips electronics N.V., Eindhoven (NL)

( * ) Notice: Subject to any disclaimer, the term of this patent is extended or adjusted under 35 U.S.C. 154(b) by 729 days.

(21) Appl. No.: 10/542,829

(22) PCT Filed: Dec. 10, 2003

(86) PCT No.: PCT/IB03/06310

§ 371 (c)(1),
(2), (4) Date: Jul. 20, 2005

(87) PCT Pub. No.: WO2004/064639

PCT Pub. Date: Aug. 5, 2004

(65) Prior Publication Data

US 2006/0116566 A1    Jun. 1, 2006

(30) Foreign Application Priority Data

Jan. 20, 2003 (EP) .................................. 03100096

(51) Int. Cl.
*H05G 1/64* (2006.01)
*G21K 4/00* (2006.01)

(52) U.S. Cl. .................... 378/98.2; 378/98.8; 378/190
(58) Field of Classification Search ................ 378/98.2, 378/98.8, 190
See application file for complete search history.

(56) References Cited

U.S. PATENT DOCUMENTS

| 3,702,935 | A | * | 11/1972 | Carey et al. | 378/189 |
| 3,925,675 | A | * | 12/1975 | Gulbis et al. | 250/485.1 |
| 4,142,101 | A | * | 2/1979 | Yin | 250/363.01 |
| 4,674,107 | A | * | 6/1987 | Urban et al. | 378/98 |
| 5,551,428 | A | | 9/1996 | Godlewski et al. | |
| 6,282,264 | B1 | * | 8/2001 | Smith et al. | 378/189 |
| 2001/0048584 | A1 | | 12/2001 | Rosen | |

FOREIGN PATENT DOCUMENTS

| WO | WO 00/31586 A1 | 6/2000 |
| WO | WO 01/80210 A1 | 10/2001 |

* cited by examiner

*Primary Examiner*—Edward J Glick
*Assistant Examiner*—Thomas R Artman

(57) ABSTRACT

The invention refers to a medical imaging device (1) comprising an X-ray source (2) for irradiating an object to be imaged. Detector means (3) having an adjustable orientation detect the X-rays after passage through the object. Conversion means convert the detected X-rays into image data. Processing means (4) process the image data, that are displayed on display means (5) having an adjustable orientation. Means (8) are provided for rendering the orientation of the detector means and the orientation of the display means essentially equal, thus enhancing the efficiency of use of the display area.

10 Claims, 1 Drawing Sheet

Figure 1:
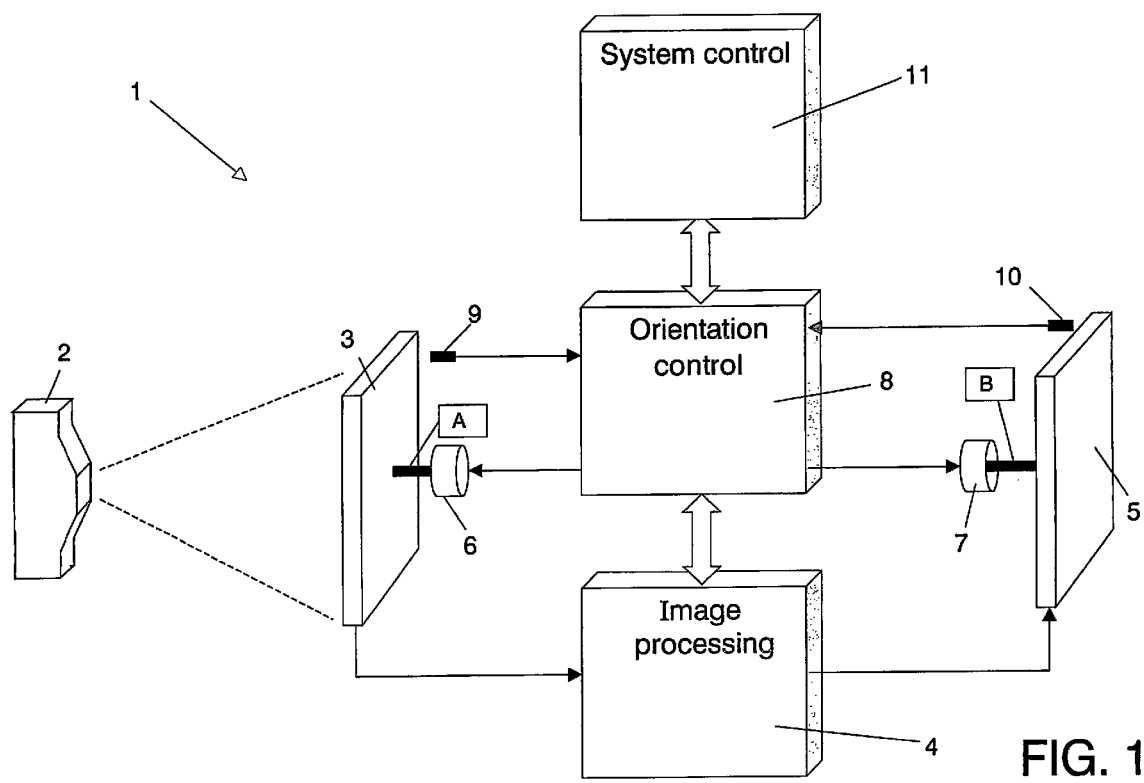

MEDICAL IMAGING DEVICE HAVING MEANS FOR RENDERING THE DETECTOR ORIENTATION AND THE DISPLAY ORIENTATION ESSENTIALLY EQUAL

The present invention relates to a medical imaging device, comprising an X-ray source for providing an X-ray image of an object, an X-ray detector to derive image data from said X-ray image and display means for displaying the image data.

Many varieties of such a medical imaging device for imaging patient data for medical purposes are known in practice. In the known systems the orientation of both the detector and the display is stationary. The detector either has a portrait or a landscape orientation depending on the medical application. Typically the display has a portrait orientation.

The known system has the disadvantage that in a considerable number of medical examinations a sub-optimal use is made of the display area for displaying the image data. For example, in case the examination was performed in the landscape orientation of the detector and the resulting image data are displayed on the stationary display screen having a portrait orientation, less than 60% of the display area is used, assuming that the detector and the display both have a 3:4 aspect ratio.

It is an object of the invention to provide a device of the type as described above that solves this problem.

The medical imaging device according to the invention is therefore characterized in that the X-ray detector has an adjustable detector orientation relative to the object, the display means have an adjustable display orientation relative to a viewer, and orientation control means are provided for rendering the detector orientation and the display orientation essentially equal.

By allowing the display means to be adjusted to the same orientation as the detector means always a 100% efficient use of the screen area is made resulting in a maximum image quality and enhanced viewer comfort.

It is noted that a display screen that is adjustable between a portrait and a landscape orientation is known per se, for instance from US 2001/0048584.

In a first preferred embodiment of the device according to the invention the orientation control means are arranged for automatically coupling the detector orientation and the display orientation. An automated coupling assures an equal orientation of both the detector and the display.

In second preferred embodiment the orientation control means are arranged for automatically providing a signal to the viewer in case the detector orientation and the display orientation are different. The viewer has to decide whether or not the display orientation needs to be adjusted in order to enhance the efficiency of use of the display screen. This embodiment is especially useful in a safety critical environment wherein automatic movement of medical equipment is undesirable.

In a practical embodiment of both the first and the second preferred embodiments the orientation control means comprise means for detecting the detector orientation and/or means for detecting the display orientation. Preferably the orientation control means are arranged to compare the detector orientation to the display orientation.

In the first preferred embodiment the detector orientation may be leading and the orientation control means are arranged for automatically adjusting the display orientation such that it is essentially equal to the detector orientation. Alternatively the display orientation may be leading and the orientation control means are arranged for automatically adjusting the detector orientation such that it is essentially equal to the display orientation. In both embodiments advantageously the operator (or the viewer) of the medical imaging device can also either control the display orientation by changing the detector orientation or vice versa.

In the second preferred embodiment preferably the signal comprises a message on the display means indicating that the display means need to be adjusted. The viewer may decide whether or not to act upon such a message in the given circumstances.

In a further detailed embodiment the processing means are arranged for controlling the coupling means. Advantageously the processing means select the optimal detector orientation and also automatically assure or signal the optimal display orientation.

The invention will be further explained by means of the attached drawing, in which:

FIG. 1 schematically shows a first preferred embodiment of the medical imaging device according to the invention.

FIG. 1 schematically shows a medical imaging device 1 according to the invention. The invention is directed to a medical imaging system in general. As an example device 1 is a diagnostic or interventional X-ray system, such as a Universal Radiography and Fluoroscopy (URF) system. Device 1 comprises an X-ray source 2 for irradiating an object to be imaged, notably a human patient (not shown). A detector 3 is located behind the object for detecting the X-rays after passage through the object. Conversion means for converting the detected X-rays into image data are provided. The conversion means are not shown as they are typically comprised in the detector. The image data are send to processing means 4 for processing the image data. The resulting processed image data are shown on display means 5. Such a system is well known in the relevant field for imaging patient data for medical purposes.

Detector 3 is rotatable around axis A by means of a motor 6. Display 5 is rotatable around axis B by means of a motor 7. Orientation control means 8 are arranged to render the detector and the display orientation essentially equal. To this end the orientation control means 8 control the motors 6 and 7. Typically the detector 3 and the display 5 are rotatable between a portrait and a landscape orientation. It is noted that the detector orientation is defined with respect to the object to be imaged, for example a patient on a patient table, whereas the display orientation is defined with respect to the viewer, which will generally be a medically skilled person.

Detector 3 is an asymmetrical detector having an aspect ratio of for instance 3:4, which is commonly used in the relevant field. The detector is preferably flat and may be of any type, such as an LCD detector or a TFT detector.

Display screen 5 is an asymmetrical display also having an aspect ratio of for instance 3:4, which is commonly used in the relevant field. The display may be a clinical CRT display as well as flat panel display or any other type of display.

In device 1 the orientation control means 8 are arranged for coupling the rotation of the detector means 3 and the display means 5. A sensor 9 is located in the vicinity of detector 3 to detect the orientation of detector 3. A sensor 10 is located in the vicinity of display 5 to detect the orientation of display screen 5. Sensors 9 and 10 may be position sensors or proximity sensors or any type of sensors that are known per se in the relevant field.

The signals of sensors 9, 10 are transmitted to the orientation control means 8. For example the orientation control means 8 may be arranged such that in case sensor 9 (or 10) detects the presence of detector 3 (or display 5) it is assumed that detector 3 (or display 5) has a portrait orientation. In case sensor 9 (or 10) detects the absence of detector 3 (or display 5) it is assumed that detector 3 (or display 5) has a landscape orientation. If necessary an additional sensor may added to sensor 9 (and sensor 10) at a position that is 90 degrees rotated with respect to the position of sensor 9 (and sensor 10) such that the assumed orientation of the detector (or display) can be confirmed.

The detector orientation is compared to the display orientation. If the orientations are different the orientation control means act to render the orientations essentially equal.

In a first mode of operation a fully automated coupling is provided wherein the orientation control means 8 are arranged for automatically coupling the detector orientation and the display orientation. In the fully automated mode the orientation control means 8 operate under control of the processing means 4.

Some medical examinations are performed in portrait orientation of the detector, such as medical examination of the spine. In case of spine examination the processing means 4 automatically control the orientation control means 8 for rotation of the detector 3 to the portrait orientation. The orientation control means 8 also operate under control of the processing means 4 to automatically rotate the display screen 5 to the portrait orientation. Other medical examinations are performed in landscape orientation of the detector, such as medical examination of the pelvis. In the above explanation "landscape" should then be read instead of "portrait".

In a second mode of operation a semi-automated coupling is provided, wherein the orientation control means 8 are arranged for rotating the detector 3, respectively the display 5, after detecting a difference in orientation with the display 5, respectively the detector 3.

For example, the detector orientation may be leading. Each time a difference in between the detector orientation and the display orientation is detected the orientation control means 8 automatically rotate the display 5 to render the display orientation essentially equal to the detector orientation. This way the operator of device 1 can control the display orientation by changing the detector orientation.

Alternatively the display orientation may be leading. The operator of device 1 can now control the detector orientation by changing the display orientation. Upon detection of a difference between detector and display orientation hereto the orientation control means 8 are arranged to automatically rotate the detector 3 to render the detector the same orientation as the display.

Changing the detector orientation and/or the display orientation can either be performed manually or by means of system control 11. In the latter case the orientation control means 8 may operate under control of the system control means 11. To this end the present detector and/or display orientation is communicated to the system control means 11.

It is noted that for safe operation a safety system can be used to monitor and interrupt the movement of the automatically rotating detector and/or display. Such a safety system is known per se in the relevant field and is generally referred to as "bodyguard".

In an alternative embodiment instead of a (semi-) automated coupling a signal is provided to the operator (or the viewer) when a difference between the detector orientation and the display orientation is detected. An example of such a signal could be a message on the display means indicating that the display means need to be rotated. This embodiment is not shown, since it is similar to the embodiment shown in FIG. 1.

In order to perform the above functions the orientation control means 4 may comprise suitable software and/or hardware known per se to a person skilled in the art.

It is noted that by an "asymmetrical detector" (respectively display) a detector (respectively display) is meant either having an asymmetrical shape or having a symmetrical shape, but using an asymmetrical area thereof. In both situations the invention allows for a rise of 78% of efficiency of use of the display area, in case of a detector 3:4 aspect ratio. The invention is thus of course not limited to the described or shown embodiments, but generally extends to any embodiment, which falls within the scope of the appended claims as seen in light of the foregoing description and drawings.

The invention claimed is:

1. A medical imaging device comprising:
   an x-ray detector;
   a display means for displaying image data;
   an x-ray detector orientation sensor;
   a display means orientation sensor; and
   an orientation control processor, wherein said orientation control processor receives signals from said x-ray detector orientation sensor and said display means orientation sensor and sends signals to orientation control means which aligns the x-ray detector and the display means in substantially similar orientations.

2. The medical imaging device of claim 1, wherein said orientation control means includes one or more motors coupled to said x-ray detector, said display means, or both the x-ray detector and the display means.

3. The medical imaging device of claim 1, wherein said orientation control means adjusts the orientation of the display means such that it is substantially similar to the orientation of the x-ray detector.

4. The medical imaging device of claim 1, wherein said orientation control means adjusts the orientation of the x-ray detector such that is substantially similar to the orientation of the display means.

5. The medical imaging device of claim 1 further comprising a bodyguard.

6. A medical imaging device comprising:
   an x-ray detector;
   a display means for displaying image data;
   an x-ray detector orientation sensor;
   a display means orientation sensor; and
   an orientation control processor, wherein said orientation control processor receives signals from said x-ray detector orientation sensor and said display means orientation sensor and produces a signal when said x-ray detector and said display means are not in substantially similar orientations.

7. The medical imaging device of claim 6, wherein the signal produced by the processor is displayed on said display means.

8. The medical imaging device of claim 6 further comprising a means for adjusting the orientation of the x-ray detector, the display means or both the x-ray detector and the display means.

9. The medical imaging device of claim 8, wherein the adjusting means automatically adjusts the orientation of the x-ray detector, the display means or both the x-ray detector and the display means.

10. The medical imaging device of claim 8, wherein the adjusting means automatically adjusts the orientation of the x-ray detector, the display means or both the x-ray detector and the display means only after receiving confirmation from an operator.

* * * * *